US012721997B2

(12) United States Patent
Yu et al.

(10) Patent No.: US 12,721,997 B2
(45) Date of Patent: Sep. 1, 2026

(54) HAPTIC APPARATUS FOR STIMULATING USERS' SKIN

(71) Applicants: City University of Hong Kong, Hong Kong (CN); The Hong Kong Polytechnic University, Hong Kong (CN)

(72) Inventors: Xinge Yu, Hong Kong (CN); Zijian Zheng, Hong Kong (CN); Kuanming Yao, Hong Kong (CN); Qiuna Zhuang, Hong Kong (CN); Qiang Zhang, Hong Kong (CN); Jingkun Zhou, Hong Kong (CN)

(73) Assignees: City University of Hong Kong, Hong Kong (CN); The Hong Kong Polytechnic University, Hong Kong (CN)

( * ) Notice: Subject to any disclaimer, the term of this patent is extended or adjusted under 35 U.S.C. 154(b) by 120 days.

(21) Appl. No.: 18/974,954

(22) Filed: Dec. 10, 2024

(65) Prior Publication Data

US 2026/0158265 A1 Jun. 11, 2026

(51) Int. Cl.

| | |
|---|---|
| ***A61N 1/04*** | (2006.01) |
| ***A61N 1/36*** | (2006.01) |
| ***G08B 6/00*** | (2006.01) |
| ***H05K 1/02*** | (2006.01) |
| ***H05K 1/09*** | (2006.01) |
| ***H05K 1/11*** | (2006.01) |

(52) U.S. Cl.

CPC ......... *A61N 1/0476* (2013.01); *A61N 1/0496* (2013.01); *A61N 1/36034* (2017.08); *G08B 6/00* (2013.01); *H05K 1/0298* (2013.01); *H05K 1/092* (2013.01); *H05K 1/115* (2013.01); *A61N 1/0484* (2013.01); *H05K 2201/09563* (2013.01)

(58) Field of Classification Search

None

See application file for complete search history.

(56) References Cited

U.S. PATENT DOCUMENTS

| | | | | |
|---|---|---|---|---|
| 9,956,393 | B2 * | 5/2018 | Perez | A61N 1/0492 |
| 10,079,391 | B2 * | 9/2018 | Kjeang | H01M 4/8605 |
| 11,786,150 | B1 * | 10/2023 | Mujeeb-U-Rahman | A61B 5/0004 600/347 |

OTHER PUBLICATIONS

M. Ying, A. P. Bonifas, N. Lu, Y. Su, R. Li, H. Cheng, A. Ameen, Y. Huang, J. A. Rogers, Silicon nanomembranes for fingertip electronics. Nanotechnology 23, 344004 (2012).

A. Withana, D. Groeger, J. Steimle, "Tacttoo: A thin and feel-through tattoo for on-skin tactile output" in UIST 2018—Proceedings of the 31st Annual ACM Symposium on User Interface Software and Technology (2018), pp. 365-378.

(Continued)

*Primary Examiner* — Carlos Garcia

(74) *Attorney, Agent, or Firm* — S&F/WEHRW

(57) ABSTRACT

A haptic apparatus is provided for stimulating a skin of a user to provide haptic feedback to the user. The haptic apparatus comprises an elastomeric substrate layer and multilayered electrical circuits comprising hydrogel electrodes for contacting the skin and electro-stimulating the skin to generate the haptic feedback. The multilayered electrical circuits are arranged on the elastomeric substrate layer, thereby avoiding forming the multilayered electrical circuits on a printed circuit board.

20 Claims, 12 Drawing Sheets

(56) References Cited

OTHER PUBLICATIONS

A. Akhtar, J. Sombeck, B. Boyce, T. Bretl, Controlling sensation intensity for electrotactile stimulation in human-machine interfaces. Science Robotics 3, eaap9770 (2018).
B. Xu, A. Akhtar, Y. Liu, H. Chen, W. H. Yeo, S. Park, B. Boyce, H. Kim, J. Yu, H. Y. Lai, S. Jung, Y. Zhou, J. Kim, S. Cho, Y. Huang, T. Bretl, J. A. Rogers, An Epidermal Stimulation and Sensing Platform for Sensorimotor Prosthetic Control, Management of Lower Back Exertion, and Electrical Muscle Activation. Advanced Materials 28, 4462-4471 (2016).
Y. Shi, F. Wang, J. Tian, S. Li, E. Fu, J. Nie, R. Lei, Y. Ding, X. Chen, Z. L. Wang, Self-powered electro-tactile system for virtual tactile experiences. Science Advances, 1-11 (2021).
Y. Tanaka, A. Shen, A. Kong, P. Lopes, "Full-hand Electro-Tactile Feedback without Obstructing Palmar Side of Hand" in Proceedings of the 2023 CHI Conference on Human Factors in Computing Systems (Association for Computing Machinery, New York, NY, USA, 2023; https://dl.acm.org/doi/10.1145/3544548.3581382)CHI '23, pp. 1-15.
S.-Y. Teng, A. Gupta, P. Lopes, "Haptic Permeability: Adding Holes to Tactile Devices Improves Dexterity" in CHI '24 (Honolulu, HI, USA, 2024).
W. Lin, D. Zhang, W. W. Lee, X. Li, Y. Hong, Q. Pan, R. Zhang, G. Peng, H. Z. Tan, Z. Zhang, L. Wei, Z. Yang, Super-resolution wearable electrotactile rendering system. Science Advances 8, eabp8738 (2022).
Y. Luo, C. Liu, Y. J. Lee, J. DelPreto, K. Wu, M. Foshey, D. Rus, T. Palacios, Y. Li, A. Torralba, W. Matusik, Adaptive tactile interaction transfer via digitally embroidered smart gloves. Nat Commun 15, 868 (2024).

* cited by examiner

HAPTIC APPARATUS FOR STIMULATING USERS' SKIN

FIELD OF THE DISCLOSURE

The present disclosure generally relates to haptic apparatus for stimulating users' skin.

BACKGROUND

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

Permeable, soft, and stretchable integrated haptic systems possessing continuous sensing and intervention abilities and wearing comfort are of particular interests for a broad range of emerging applications, such as intensive care, rehabilitation, close-loop diagnosis/treatment, and virtual reality/augmented reality. In the past two decades, enormous progress has been made in developing novel materials and architectures for haptic electronics.

New apparatus or systems that assist in advancing technological needs and industrial applications in haptic electronics are desirable.

SUMMARY

In accordance with certain embodiments, there is provided a haptic apparatus for stimulating a skin of a user to provide haptic feedback to the user. The haptic apparatus comprises an elastomeric substrate layer and multilayered electrical circuits. The multilayered electrical circuits comprise hydrogel electrodes for contacting the skin and electrostimulating the skin to generate the haptic feedback. The multilayered electrical circuits are arranged on the elastomeric substrate layer, thereby avoiding forming the multilayered electrical circuits on a printed circuit board.

In certain embodiments, the multilayered electrical circuits are monolithically formed on the elastomeric substrate layer. The elastomeric substrate layer may comprise an elastomeric fiber mat.

In certain embodiments, the multilayered electrical circuits comprise patterned liquid metal (LM) traces.

In certain embodiments, the hydrogel electrodes comprise LM pads disposed on the patterned LM traces and a bioadhesive hydrogel disposed on the LM pads for establishing an electrically conducive path to the skin.

In certain embodiments, the hydrogel electrodes comprise a paste mask layer sandwiched between the LM pads and the bioadhesive hydrogel. The paste mask layer is configured to allow the bioadhesive hydrogel to penetrate at least partially through the paste mask layer, thereby contacting the LM pads. The paste mask layer may comprise fiber mat.

In certain embodiments, the multilayered electrical circuits comprise: a first circuit layer comprising first patterned liquid metal (LM) traces, a second circuit layer comprising second patterned LM traces, and LM interconnects for electrically connecting the first circuit layer and the second circuit layer.

In certain embodiments, the LM interconnects comprise vertical interconnect accesses (VIAs). The VIAs comprise fluidic LM for electrically contacting both the first patterned LM traces and the second patterned LM traces.

In certain embodiments, the multilayered electrical circuits comprise electronic components disposed on the second circuit layer, and the electronic components electrically contact the second patterned LM traces through hybrid LM (hLM) solders.

In certain embodiments, the hLM solders comprise fluidic LM electrically contacting the electronic components, and an oxidized LM (oLM) paste sandwiched between the fluidic LM and the second patterned LM traces, thereby to electrically connect the electronic components to the second circuit layer.

In certain embodiments, the haptic apparatus comprises an elastomeric encapsulation layer for at least partially encapsulating the multilayered electrical circuits. The elastomeric encapsulation layer may comprise an elastomeric fiber mat.

In certain embodiments, the hydrogel electrodes comprise a plurality of channels, and the multilayered electrical circuits comprise a control circuit for generating pulsed voltage signals for feeding into the plurality of channels for stimulating the skin of the user.

In certain embodiments, the control circuit comprises: a power management module for generating a regulated voltage; a voltage booster module for boosting up the regulated voltage to yield a boosted voltage; a plurality of multiplexers for controllably switching on and off the boosted voltage to generate pulsed voltage signals; and a microcontroller unit (MCU) configured to at least control the plurality of multiplexers in switching the boosted voltage for generating an individual pulsed voltage signal with a desired pulse frequency and a desired duty cycle.

In certain embodiments, the power management module comprises a battery for providing a battery supplied electrical voltage, and a regulator for regulating the battery supplied electrical voltage to the regulated voltage.

In certain embodiments, the battery is a rechargeable battery. The power management module further comprises a QI wireless charging module for recharging the rechargeable battery.

In certain embodiments, the control circuit further comprises a current control module controllable by the MCU for monitoring and limiting a return current received by a common electrode from the user to avoid the user from getting an electric shock.

In certain embodiments, the current control module comprises a current mirror that electrically connects to the MCU through either an operational amplifier or a digital-to-analog converter.

In certain embodiments, the hydrogel electrodes have a highest electrode density of 2.26 units/cm$^2$.

Other example embodiments are discussed herein.

BRIEF DESCRIPTION OF THE DRAWINGS

The detailed description is set forth with reference to the accompanying drawings. The drawings are provided for purposes of illustration only and merely depict example embodiments of the disclosure. The drawings are provided to facilitate understanding of the disclosure and shall not be deemed to limit the breadth, scope, or applicability of the disclosure. The drawings are not to scale, unless otherwise disclosed. Certain parts of the drawings are exaggerated for explanation purposes and shall not be considered limiting unless otherwise specified.

DETAILED DESCRIPTION

Figure 1A:
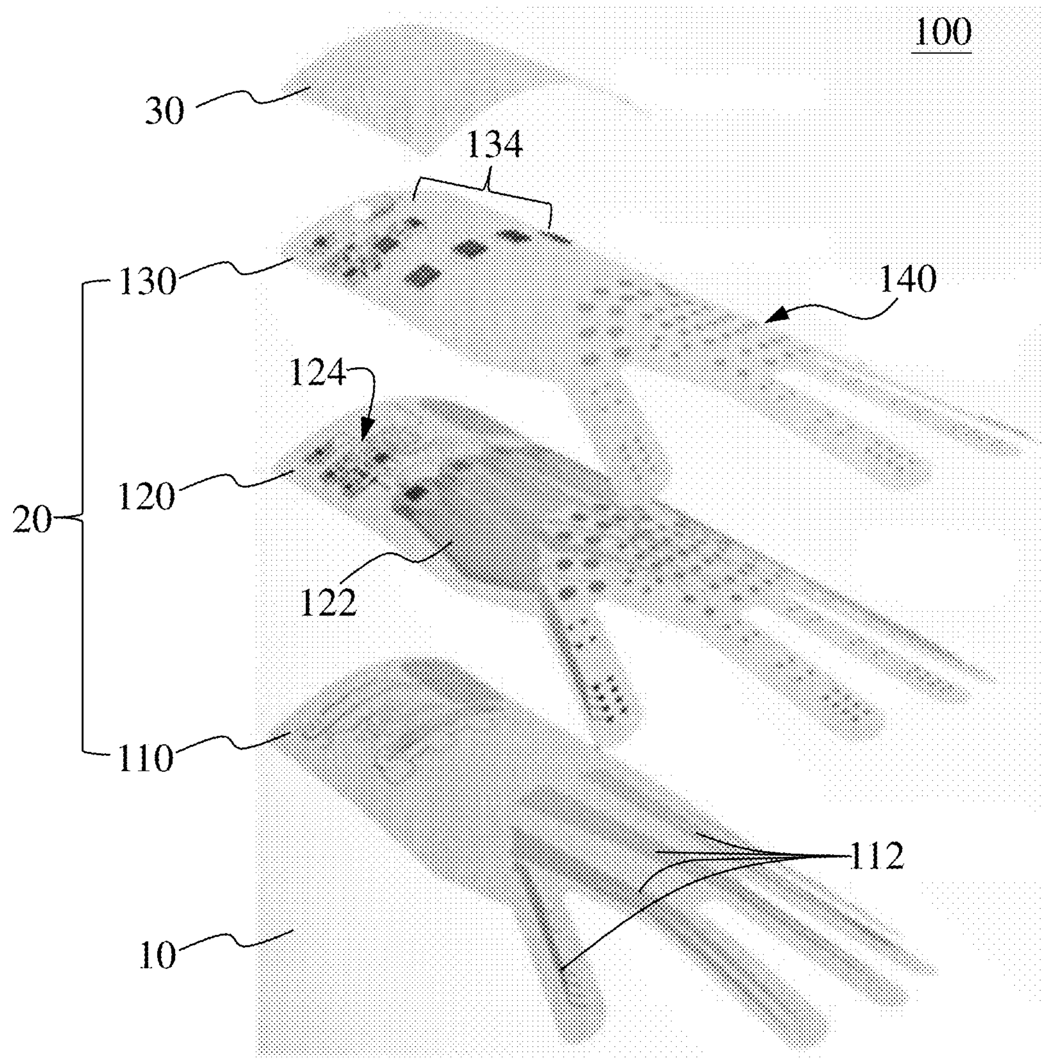
FIG. 1A is a schematic illustration of an exploded view of a haptic apparatus in accordance with certain embodiments of the present disclosure.

The present disclosure will now be described with reference to the following examples which should be considered in all respects as illustrative and non-restrictive.

Throughout the description and the claims, the words "comprise", "comprising", and the like are to be construed in an inclusive sense as opposed to an exclusive or exhaustive sense; that is to say, in the sense of "including, but not limited to".

Furthermore, as used herein and unless otherwise specified, the use of the ordinal adjectives "first", "second", etc., to describe a common object, merely indicate that different instances of like objects are being referred to, and are not intended to imply that the objects so described must be in a given sequence, either temporally, spatially, in ranking, or in any other manner.

Example embodiments relate to haptic apparatus for stimulating users'skin.

Many existing haptic apparatus or systems for stimulating users'skin are unsatisfactory in one aspect or another. Their disadvantages comprise, for example, low spatial resolution, cumbersome and bulky design by including wiring adaptors, connectors, flexible flat cables (FFC), and/or external fixation, glue or adhesive tapes. Further, the electronics of the existing apparatus or systems are often formed on one or more rigid or flexible printed circuit boards (PCBs).

Example embodiments solve one or more of these problems and provide technical solutions with novel design and improved performance as described herein with one or more embodiments.

One or more embodiments provide a haptic apparatus for stimulating a skin of a user to provide haptic feedback to the user. The haptic apparatus comprises an elastomeric substrate layer and multilayered electrical circuits comprising hydrogel electrodes for contacting the skin and electrostimulating the skin to generate the haptic feedback. The multilayered electrical circuits are arranged on the elastomeric substrate layer, thereby avoiding forming the multilayered electrical circuits on a printed circuit board.

According to one or more embodiments, the haptic apparatus is implemented as a breathable bioadhesive soft wearable haptic interface (BWHI) which can adhere to the user's hand and provide precise and stable haptic feedback even during sports or sweating. The haptic interface is formed as a monolithically integrated system and thin, soft, stretchable. When worn on a user's hand, the haptic interface can hardly be felt by the user when doing activities. The excellent breathability and wearing comfort help the skin to maintain good thermal equilibrium.

According to one or more embodiments, the BWHI is a flexible device integrated in one-piece, which can provide haptic feedback to the whole hand and does not impede normal skin perspiration. The BWHI features a large area, high resolution electrotactile electrodes array that empowers precise dynamic feedback on the hand. In one or more embodiments, the BWHI utilizes permeable elastomeric polymer fiber mat as the elastomeric substrate layer and thereby ensures excellent permeability to air and moisture. This allows sweat to evaporate and thereby keeps skin dry and comfortable during use and prevents skin from itchiness or inflammation.

According to one or more embodiments, there is provided a complete system and skin interface integrally formed as a single piece comprising a permeable elastomeric fiber mat, liquid metal (LM) traces or circuits, and bioadhesive hydrogels. The skin interface is ultra-soft, stretchable and can adhere firmly to the skin, thereby adapting to natural hand motions. It achieves high overall and highest electrode densities (~1 and ~2.26 units/cm$^2$ respectively), thereby resulting in improved spatiotemporal resolution for dynamic feedback that remains unaffected by sweating. As used herein, the term "overall electrode density" refers to the numbers of electrodes per unit area on the whole hand (palm and fingers) coverage area, and the term "highest electrode density" refers to the local value of this density at the densest place (such as fingertip). In terms of permeability, stretchability, adhesiveness, and system-level integrality, the skin interface according to one or more embodiments outperforms existing haptic wearables, thereby making haptics more comfortable and closer to real experiences.

According to one or more embodiments, the haptic apparatus is exemplified as a BWHI or BWHI system that is implemented as a one-piece, stand-alone haptic interface system. With multilayer wireless electronics system parts and a high-density (e.g., 128 units over the palm) electrodes array monolithically fabricated on a same substrate, no external cables, connectors, or wires are needed for the BWHI to work; rather, to be workable, a user can simply place or wear a piece of fully functional electronic textile onto his/her hand. This is advantageous over many existing systems in which two or more separate and independent parts are provided on separate PCBs and interconnected by external cables (such as flat flexible cables) and no greater than 32 feedback units can be provided on the palm. The BWHI as described herein according to one or more embodiments provides significantly improved spatial resolution for fine recognizing because of factors, such as provision of a significantly increased number of feedback units and usage of only internally embedded interconnections.

According to one or more embodiments, there are provided various spatiotemporal dynamic modes of electrotactile haptic feedback for the haptic apparatus. The present inventors have found that the haptic feedback based on the dynamic modes outperforms the static feedback with consistent current parameters in terms of user's identification rate. Further, the breathable nature of the haptic apparatus prevents the sweat from accumulating in the interface and avoids sensation distortion and the dramatic drop of the identification rate. This is advantageous over many existing systems in which only static feedback is provided on individual feedback unit and the resultant sweat leads to loosening or detachment of electrodes and distorting the haptic sensation.

According to one or more embodiments, owning to the fibrous electrospun elastomeric fiber mat, which functions as the matrix material of both substrate and encapsulation, the haptic apparatus owns high permeability for moisture and air, and thus helps the user's hand to maintain normal thermal equilibrium and feel dry and comfortable even with perspiration in sports or long-term wearing. This is advantageous over many existing systems in which the substrate of the hand patch electrodes array is impermeable, which leads to sweating and discomfort.

According to one or more embodiments, with routing circuit traces made of liquid metal (e.g., EGaIn), the substrate made of elastomeric rubber and interfacial electrodes made of hydrogel, the haptic apparatus is completely soft and stretchable (up to 500%), which endows the haptic apparatus with high flexibility that can easily adapt to the deformation of the skin, thereby ensuring the unaffected dexterity of the hand. This is advantageous over many existing systems in which the conducting traces include copper for circuits and gold for the electrodes) and can work under at most 20% strain.

According to one or more embodiments, by engineering the composition of the hydrogel as the skin-interfacing electrodes or skin electrodes, the electrodes are not only conductive but also bioadhesive with exceptional and durable peel-off strength (~100 N/m) that allows the haptic apparatus to adhere firmly to the skin without additional fixation during use, even when the hand is posing gestures with large-scale deformation. Therefore, the electrode-skin interface remains stable in movements and ensures consistency of the haptic feedback. This is advantageous over many existing systems in which the adhesion strength is weaker and needs external fixation. Thus, the haptic apparatus according to one or more embodiments has a wider range of applications, particularly advantageous over the existing systems when used in intense sports, long-term use, or large-scale movements.

The haptic apparatus according to one or more embodiments offers various advantages, such as one or more of the followings: high permeability/stretchability allowing skin to breathe and deform, bio-adhesiveness that ensures stable skin-electrodes interface, and high integration level and electrodes density that renders fine dynamic haptic information with high resolution. The excellent permeability improves conform greatly when worn on users' hand. To enhance permeability and flexibility, the present inventors have discarded the rigid/flexible printed circuit board (PCB/fPCB)-based haptic system, and innovatively form electrical circuits on the fiber mat using patterned LM traces without using any PCB. The entire system can be fabricated in a one-piece, stacked multi-layer fashion. In one or more embodiments, conductive and bio-adhesive hydrogel pieces are cured on top of the LM electrode sites and can be firmly adhered to the skin, forming a low-impedance electrode-skin interface serving as the electrotactile current pathway that keeps steady without external support and even under deformation.

According to one or more embodiments, the haptic apparatus offers one or more of the following advantages: (1) much denser electrodes array (1 and 2.26 units/cm$^2$ for overall and highest density respectively) with multiplied feedback units. This enables the apparatus to provide feedback with much higher spatial resolution, especially for presenting dynamic pattern/texture changes within a small area; (2) monolithic integration of both electronic systems and stimulator units on a one-piece stretchable soft substrate. With this configuration, no external wiring adaptors, connectors or flexible flat cables are needed for connecting electronics part and stimulator part; (3) excellent breathability. As the fiber mat is permeable to air and moisture, the skin covered by the apparatus can still breathe as bared and maintain the normal thermal equilibrium, thereby avoiding skin occlusion (the skin occlusion can lead to inflammations, finger and hand pain, erythema and onycholysis); (4) bioadhesiveness. With bioadhesive hydrogel as the stimulating electrode, the whole apparatus can tightly adhere to the skin without any external fixation, such as glue or adhesive tapes. This also ensures that the interface is kept conformal to the skin while the apparatus is deformed. To the present inventors' best knowledge, there is no wearable device available on the market that can provide satisfying breathability, strong adhesion to skin, whole hand coverage, high resolution dynamic feedback and skin-like softness at the same time.

The haptic apparatus according to one or more embodiments has multiple applications in the field of wearable electronics, entertainment, industry, and clinical care, etc. One application can be to provide haptic feedback for users in virtual reality (VR), augmented reality (AR), mixed reality (XR), Metaverse, Apple Vision Pro or other types of interactions with virtual/digital objects. The haptic apparatus according to one or more embodiments can provide high-resolution, both static and dynamic haptic feedback to over 128 spots on the hand to reproduce the tactile information intended to present. Especially for scenarios involving sports, hot environments, intense vibe, or for use over 30 minutes, the haptic apparatus according to one or more embodiments can keep the hand dry and comfortable while perspiring, and keep it free of sweat-induced discomfort, without compromising the feedback performance.

Other example applications include teleoperation of machines, humanoid robots, robotic hands or arms, etc. The tactile information of the robotics can be collected by integrated sensors, and then encoded into perceivable haptic stimulation and finally feedback onto the operator's hand via the haptic apparatus. A further example application includes tactile reinforcement for people with dysaphia (tactile impairment). While the impaired skin cannot perceive fine or small pressure, the electrotactile provided by the haptic apparatus according to one or more embodiments can amplify the stimulation strength and make it more perceivable. The haptic apparatus according to one or more embodiments may also be used for therapeutic stimulations for assisting the rehabilitation of tactile impaired patients. The haptic apparatus according to one or more embodiments may be used in other fields, including but not limited to, healthcare and medical field (training simulations, assisted surgeries, emergency navigations, etc.), gaming and entertainment, workforce development and training, remote manufacturing, and real estate virtual showings.

FIG. 1 is a schematic illustration of an exploded view of a haptic apparatus 100 in accordance with certain embodiments of the present disclosure. The haptic apparatus 100 is configured for stimulating a skin of a user to provide haptic feedback to the user. In one or more embodiments, the haptic apparatus 100 can implemented as a BWHI and achieve one or more technical advantages as described herein.

The haptic apparatus 100 comprises an elastomeric substrate layer 10 and multilayered electrical circuits 20. The multilayered electrical circuits 20 comprises hydrogel electrodes 140 for contacting the skin and electro-stimulating the skin to generate the haptic feedback. The multilayered electrical circuits 20 are arranged on the elastomeric substrate layer 10, thereby avoiding forming the multilayered electrical circuits on a printed circuit board (PCB).

The haptic apparatus 100 can be formed or made in a one-piece, stacked multi-layer fashion. The elastomeric substrate layer 10 provide support or housing for the multilayered electrical circuits 20 and eliminate the necessity to use any PCB. The elastomeric substrate layer 10 can comprise any proper elastomeric materials, such as rubber.

By way of example, the elastomeric substrate layer 10 comprises an elastomeric fiber mat or can be an elastomeric fiber mat. The multilayered electrical circuits 20 can be monolithically formed on the elastomeric substrate layer 10, such that the haptic apparatus 100 is formed in a single piece.

The multilayered electrical circuits 20 is illustrated to comprise a first circuit layer 110, a second circuit layer 120 and a third circuit layer 130. These circuit layers comprise various electronic components (such as resistors, capacitors, transistors, IC chips, etc.) and electrical interconnections and routings. It will be understood that in some embodiments, the second and third circuit layers can be replaced with one circuit layer. In some other embodiments, the multilayered electrical circuits 20 comprises four or more circuit layers.

As illustrated in the present embodiment, the first circuit layer 110 is a bottom layer formed directly on the elastomeric substrate layer 10 and comprises liquid metal (LM) connections or LM circuits or patterned LM traces 112. The LM may comprise eutectic gallium indium alloy (EGaIn), gallium indium tin alloy (GaInSn), or a mixture thereof. The second circuit layer 120 comprises electronic components 124, and LM connections or patterned LM traces 122. The third circuit layer 130 comprises electronic components 134 and the hydrogel electrodes 140. The hydrogel electrodes 140 can comprise a large number of electrodes, such as 128 electrodes, for providing improved haptic feedback.

Note that all the electronic components on a same circuit layer can be electrically connected via patterned LM traces. The electronic components of adjacent circuit layers may be electrically connected via vertical interconnect accesses (VIAs). The VIAs can comprise LM or liquid metals (LMs) as illustrated below with one or more embodiments. All the electronics can be formed and electrically connected through the internally embedded connections. No external wires or cables are required for the haptic apparatus 100.

In the present embodiment, an elastomeric encapsulation layer 30 is provided for at least partially encapsulating the multilayered electrical circuits 20. The elastomeric encapsulation layer 30 is arranged on the third circuit layer 130 and can protect underlying components, such as electronic components and LM traces, from being scratched and thereby avoid circuit damage. In this sense, the elastomeric encapsulation layer 30 is a protective layer. The elastomeric encapsulation layer can comprise an elastomeric fiber mat. The elastomeric encapsulation layer can be porous and thin enough to allow liquid metal pastes to penetrate through it when pressed with certain force, and thus can also function as a paste mask layer. For example, after being treated by plasma, the elastomeric encapsulation layer allows uncured hydrogel to penetrate through it.

Figure 1B:
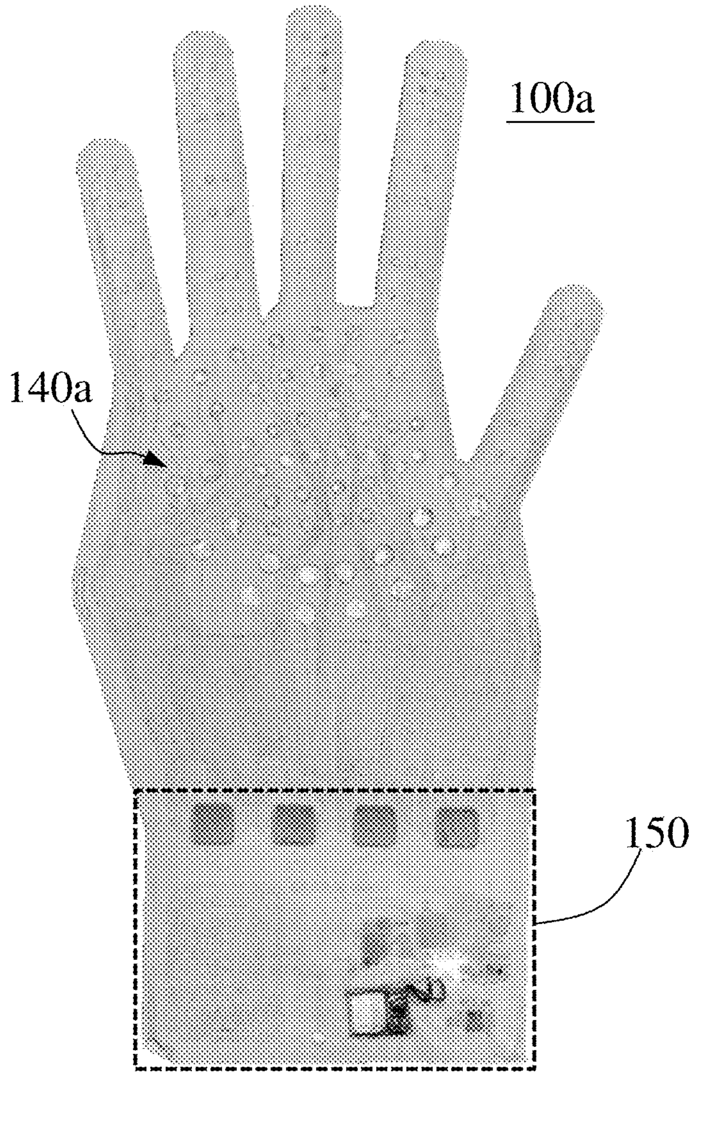
FIG. 1B is an optical photograph of a fully integrated and encapsulated haptic apparatus implemented as a breathable bioadhesive soft wearable haptic interface (BWHI) in accordance with certain embodiments of the present disclosure.

FIG. 1B is an optical photograph of a fully integrated and encapsulated haptic apparatus implemented as a breathable bioadhesive soft wearable haptic interface (BWHI) 100*a* in accordance with certain embodiments. The BWHI 100*a* can be a specific implementation of the haptic apparatus 100 of FIG. 1A. The BWHI 100*a* comprises hydrogel electrodes 140*a* forming an electrodes array and a control circuit 150 that functions as a drive unit for generating a plurality of pulsed voltage signals for driving the hydrogel electrodes 140*a* to thereby induce a plurality of excitation currents flowing into the user. As can be seen, the hydrogel electrodes 140*a* comprise a large number of electrodes that spread a large area on the palm and fingers, thereby capable of providing improved haptic feedback.

Figure 2:
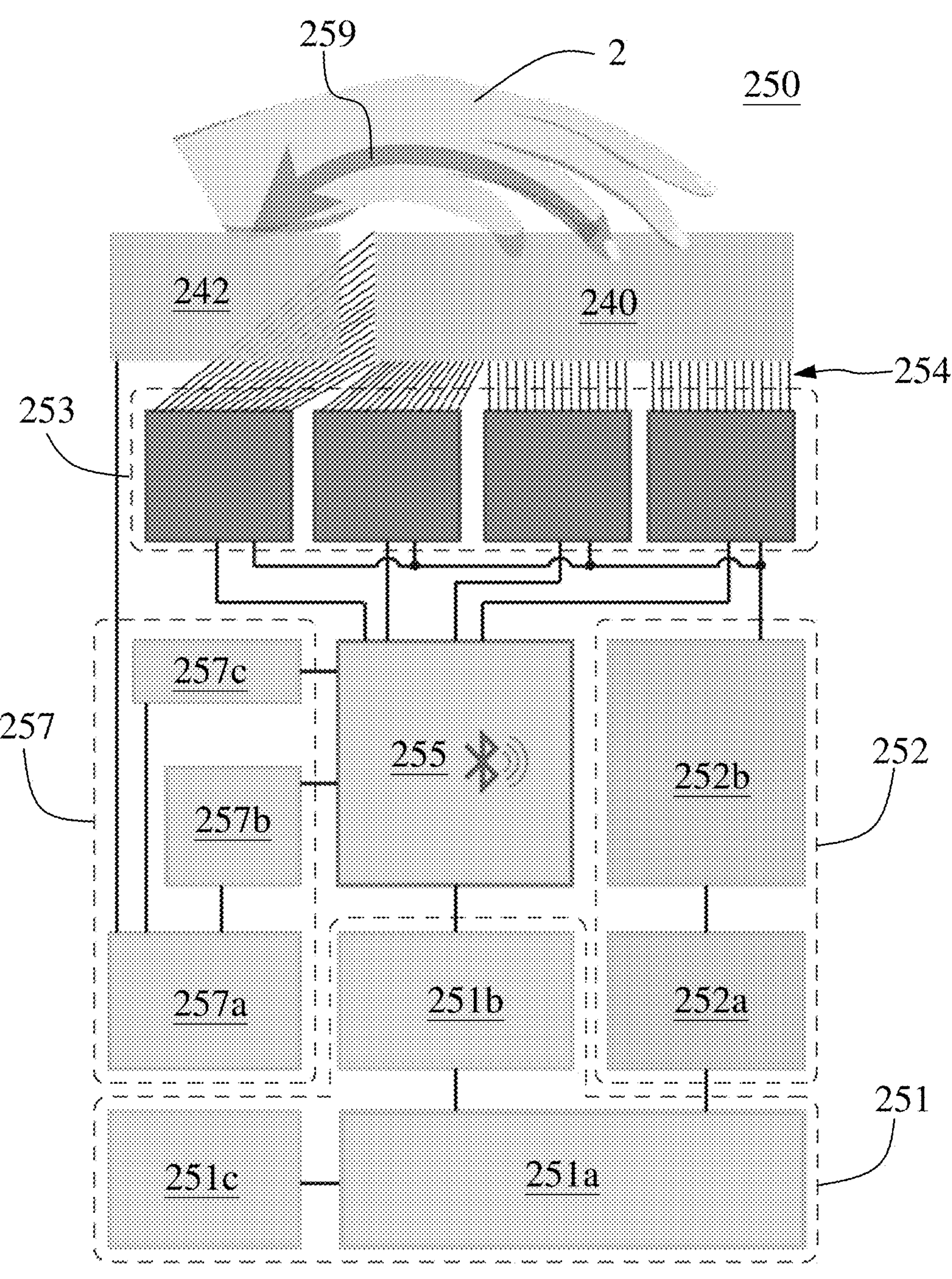
FIG. 2 is a block diagram of a control circuit of a haptic apparatus in accordance with certain embodiments of the present disclosure.

FIG. 2 is a block diagram of a control circuit 250 of a haptic apparatus in accordance with certain embodiments. The control circuit 250 can be part of the haptic apparatus 100 of FIG. 1A for driving the hydrogel electrodes 140 or a specific implementation of the control circuit 150 of FIG. 1B.

As illustrated, the control circuit 250 comprises a power management module 251 for generating a regulated voltage, a voltage booster module 252 for boosting up the regulated voltage to yield a boosted voltage, a plurality of multiplexers (MUXs) 253 for controllably switching on and off the boosted voltage to generate pulsed voltage signals, and a microcontroller unit (MCU) 255 configured to at least control the plurality of multiplexers in switching the boosted voltage for generating an individual pulsed voltage signal with a desired pulse frequency and a desired duty cycle.

The power management module 251 comprises a battery 251*a* for providing a battery supplied electrical voltage, and a regulator 251*b* for regulating the battery supplied electrical voltage to the regulated voltage. The battery 251*a* can be a rechargeable battery, such as a 3.7V Lithium-Ion battery. A wireless charging module 251 *c* in the form of a QI wireless charging module may be provided for recharging the rechargeable battery.

The voltage booster module 252 is used for boosting up the regulated voltage to yield the boosted voltage. The route from the power management module 251 to the voltage booster module 252 may be controlled by an MCU-controlled electronic switch. When the MCU 255 is started or restarted, the electronic switch is disabled (OFF) at default settings to disconnect the voltage booster module 252 from the power management module 251, and is only enabled (ON) to provide the boosted voltage when the MCU 255 receives a stimulation command. This arrangement is to prevent an unwanted electric shock to the user from occurring due to contact with a high voltage by accident when electrotactile stimulation is not yet applied.

As illustrated, the voltage booster module 252 is implemented with two voltage boosting stages. The first stage is a medium-voltage booster 252*a*, which boosts the regulated voltage to a medium level, e.g., 12V. The second stage is a high-voltage booster 252 *b*, which boosts the medium-level voltage to a high voltage (which is the boosted voltage) for stimulation. The boosted voltage can be up to 135V. The amplitude of the boosted voltage may be adjusted according to practical needs. The MUX 253 receives the boosted voltage and further transmit the boosted voltage into the user's hand 2 via respective channels 254 and hydrogel electrodes 240.

The control circuit 250 further comprises a current control module 257. The current control module 257 can be controlled by the MCU 255 for monitoring and limiting a return current received by a common electrode 242 from the user's hand 2 via a path 259 to avoid the user from getting an electric shock. The current control module 257 comprises a current mirror 257*a* that electrically connects to the MCU 255 through either an operational amplifier 257*b* or a digital-to-analog converter (DAC) 257*c*. The control circuit 250 may be compliant to one or more wireless-communication protocols, such as Bluetooth Low Energy (BLE) protocol.

One or more embodiments can realize effective electrotactile feedback in 128 sites on the hand, four high voltage multiplexing switches are deployed for distributing pulses to all these sites. The MCU controls MUXs and current control module to drive monophasic current pulses through the skin and stimulates the mechanoreceptor-associated afferent nerves. With various pre-programmed dynamic modes, it is convenient to induce different types of tactile sensations in a single site or moving patterns in multiple sites, by simply sending short commands via BLE wireless communication using a mobile device, such as a smartphone.

Figure 3A:
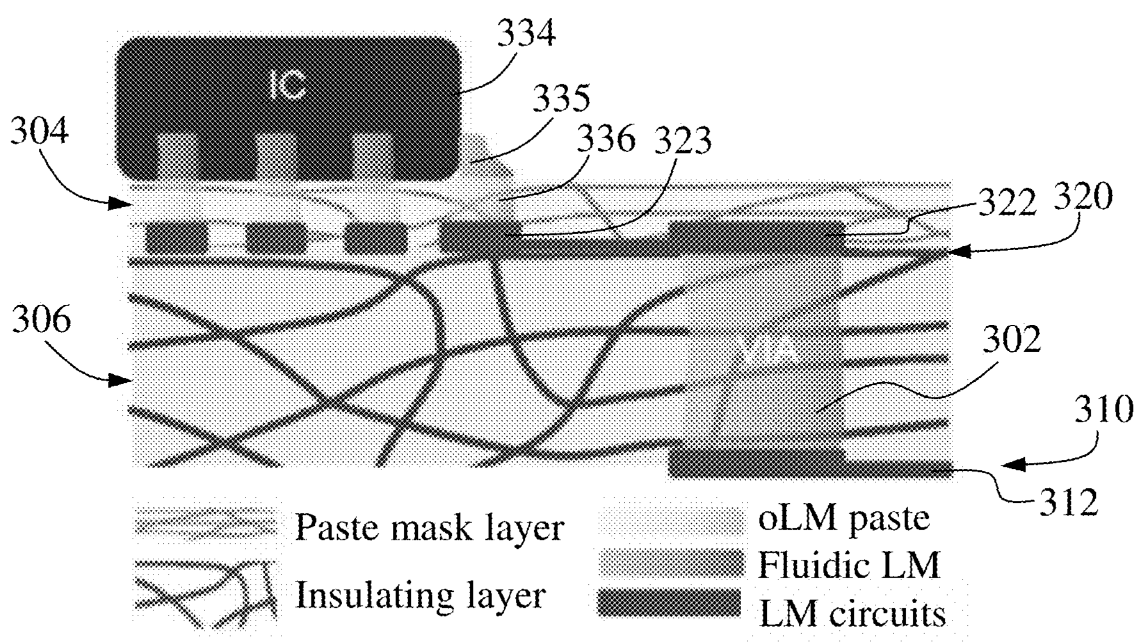
FIG. 3A is a schematic illustration of an interlayer structure of a LM (liquid metal)-based vertical interconnect access (VIA) and the soldering structure for an electronic component exemplified as an integrated circuit (IC) chip, where the soldering structure penetrates a paste mask layer, in accordance with certain embodiments of the present disclosure.

FIG. 3A is a schematic illustration of an interlayer structure of a LM-based vertical interconnect access (VIA) and the soldering structure for an electronic component exemplified as an integrated circuit (IC) chip, where the soldering structure penetrates a paste mask layer, in accordance with certain embodiments. The interlayer structure electrically connects two circuit layers of the haptic apparatus. The soldering structure electrically connects one or more electronic components to a certain circuit layer. Each of the interlayer structure and the soldering structure should be broadly understood as referring to arrangement, design, materials, or their proper modifications or variations thereof used to create an electrical connection between components, layers, etc. in the context of the present description.

As illustrated, a first circuit layer 310 comprises first LM circuits in the form of first patterned LM traces 312. A second circuit layer 320 comprises second LM circuits in the form of second patterned LM traces 322. The first circuit layer 310 and the second circuit layer 320 are separated by an insulating layer 306 (which may comprise elastomeric fiber mat) and electrically connected with each other via LM interconnects comprising VIAs. In FIG. 3A, a VIA 302 is shown for illustrative purpose only. It will be understood that there may be multiple VIAs in various embodiments. The VIA 302 comprises fluidic LM for electrically contacting both the first patterned LM traces 312 and the second patterned LM traces 322, thereby electrically connecting the first circuit layer 310 and the second circuit layer 320.

The second patterned LM traces 322 comprise LM pads 323 for connecting to various electronic components, such as the IC chip 334. The IC chip 334 is disposed on the second circuit layer 320. The IC chip 334 may be part of another circuit layer on top of the second circuit layer 320, or be part of the second circuit layer 320. The IC chip 334 electrically contacts the LM pads 323 of the second patterned LM traces 322 through hybrid LM (hLM) solders. The hLM comprises a combination of partially oxidized LM (oLM) and LM. The oLM may be prepared by oxidizing LM in the air. In the present embodiment, the hLM solders comprise fluidic LM 335 that electrically connects or contacts the IC chip 334. An oLM paste 336 is sandwiched between the fluidic LM 335 and the LM pads 323 of the second patterned LM traces 322, thereby to electrically connect the IC chip 334 to the second circuit layer 320.

In FIG. 3A, a paste mask layer 304 is provided on the second circuit layer 320 and functions as a protective layer for protecting the underlying second patterned LM traces 322. The paste mask layer 304 can comprise fiber mat, such as elastomeric fiber mat. The paste mask layer 304 can be a thin fiber mat functioning as a protective layer for the LM traces underneath (such as the second patterned LM traces 322). The oLM paste 336 can penetrate through the paste mask layer 304 for establishing electrical connection between the electronic components above and the LM traces underneath.

The present embodiment has demonstrated the effectiveness of using hybrid LM solders to solder the pins of electronic components to the LM pads. The method can work well even under severe stretching.

Figure 3B:
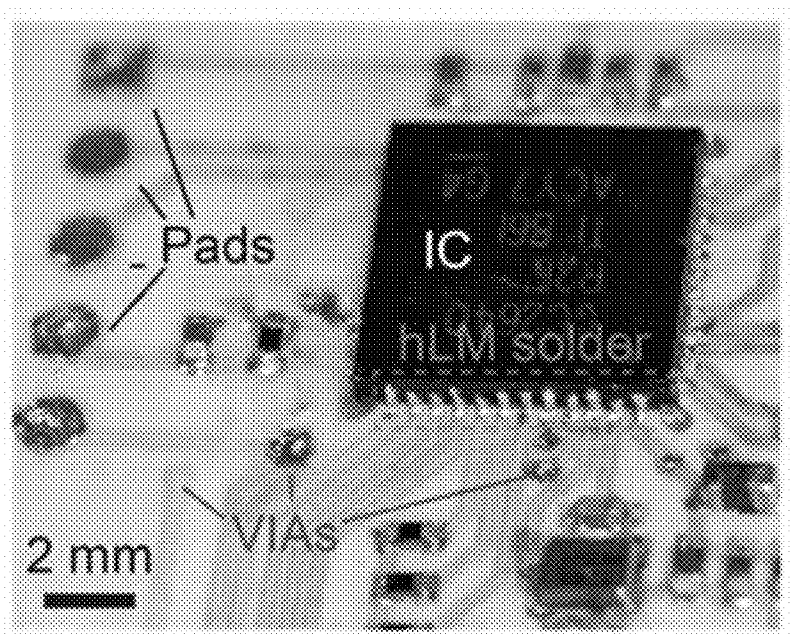
FIG. 3B is an optical photograph showing a soldered IC chip, exposed pads and vertical interconnect accesses (VIAs) in accordance with certain embodiments of the present disclosure.
Figure 3C:
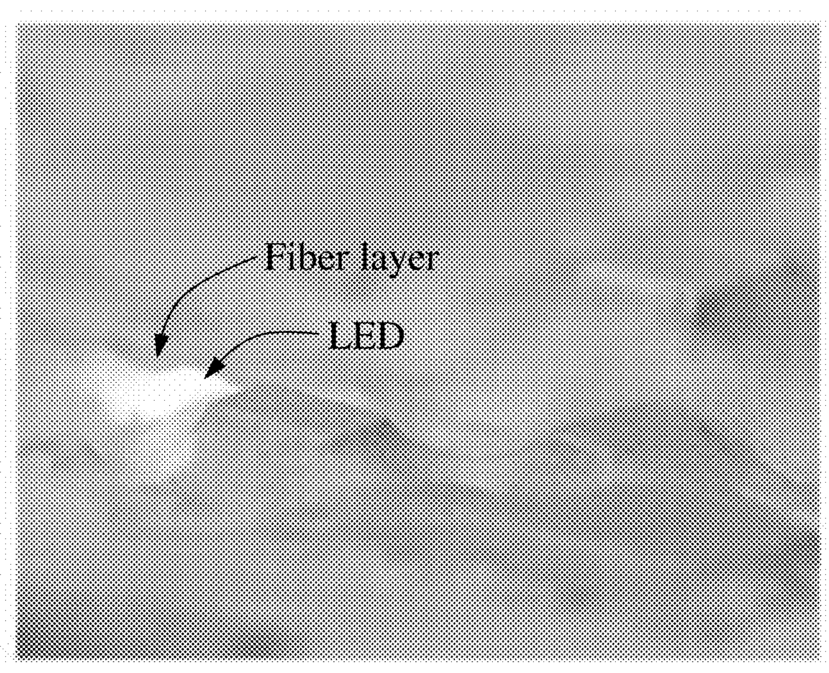
FIG. 3C is an optical photograph showing electronic components (including a glowing light-emitting diode (LED)) encapsulated under an electrospun fiber layer in accordance with certain embodiments of the present disclosure.

FIG. 3B is an optical photograph showing a soldered IC chip, exposed pads and VIAs in accordance with certain embodiments. FIG. 3C is an optical photograph showing electronic components (including a glowing LED) encapsulated under an electrospun fiber layer in accordance with certain embodiments.

According to certain embodiments, stiffness-engineered oLM paste is used to ensure stable contact with the pins of the IC chip. The pads are stencil printed on top of a thin mask (~20 μm in thickness) that protects LM traces but allows the oLM paste to penetrate through for stable electrical contact with the LM traces. VIAs made of fluidic LM guarantee inter-layer connectivity and connect the top and bottom routing layers through laser-ablated holes in the substrate (~100 μm). LM circuits can well survive skin deformations since their resistance maintains low even when being severely stretched.

Figure 3D:
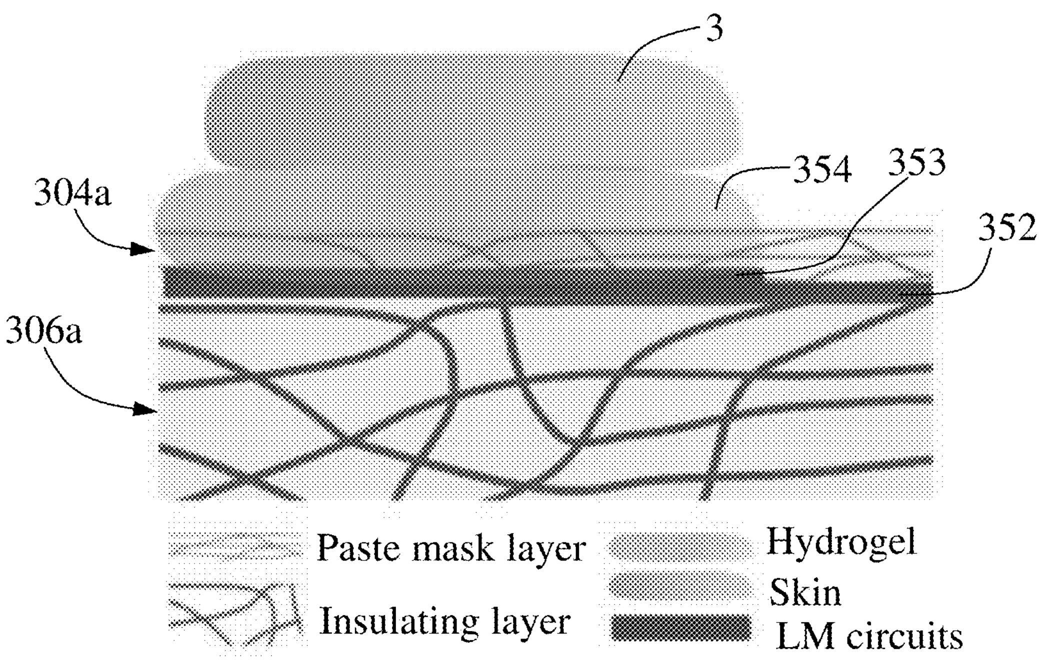
FIG. 3D is a schematic illustration showing a bioadhesive hydrogel integration structure in accordance with certain embodiments of the present disclosure.

FIG. 3D is a schematic illustration showing a bioadhesive hydrogel integration structure in accordance with certain embodiments. As illustrated, the LM circuits or LM traces 352 are formed on an insulating layer **306*a* (e.g., elastomeric fiber mat) and comprise LM pads 353. A paste mask layer 304*a* is sandwiched between the LM pads 353 and the bioadhesive hydrogel 354. The paste mask layer 304*a* may comprise fiber mat, such as elastomeric fiber mat. The paste mask layer 304*a* can be a thin fiber mat functioning as a protective layer for the LM traces 352 underneath. The paste mask layer 304*a* is configured to allow the bioadhesive hydrogel 354 to penetrate at least partially through the paste mask layer 304*a*, thereby contacting the LM pads 343**.

In operation, the bioadhesive hydrogel 354 contacts a user's skin 3. That is, the bioadhesive and conductive hydrogel functions as a LM-skin interface to deliver effective haptic feedback. By carefully engineering its composition, the hydrogel exhibits excellent stretchability, low swelling ratio that leading to smaller sweat-induced structure deformation and excellent biocompatibility and antimicrobial effects, which has demonstrated as a strong and safe bioelectrical interface. Uncured fluidic hydrogel penetrates through the fibrous network of the underlying paste mask layer, thereby establishing stable electrical contact with the LM traces through robust interfacial bonding. After in-situ ultraviolet (UV) crosslinking, the hydrogel becomes robustly fixed within the skeleton of the paste mask layer, such as the elastomeric fiber mat.

In some embodiments, the LM pads 353 and the bioadhesive hydrogel 354 together can be considered as forming the hydrogel electrodes or forming part of the hydrogel electrodes. In some other embodiments, the paste mask layer **304*a*** can also considered as part of the hydrogel electrodes.

Figure 3E:
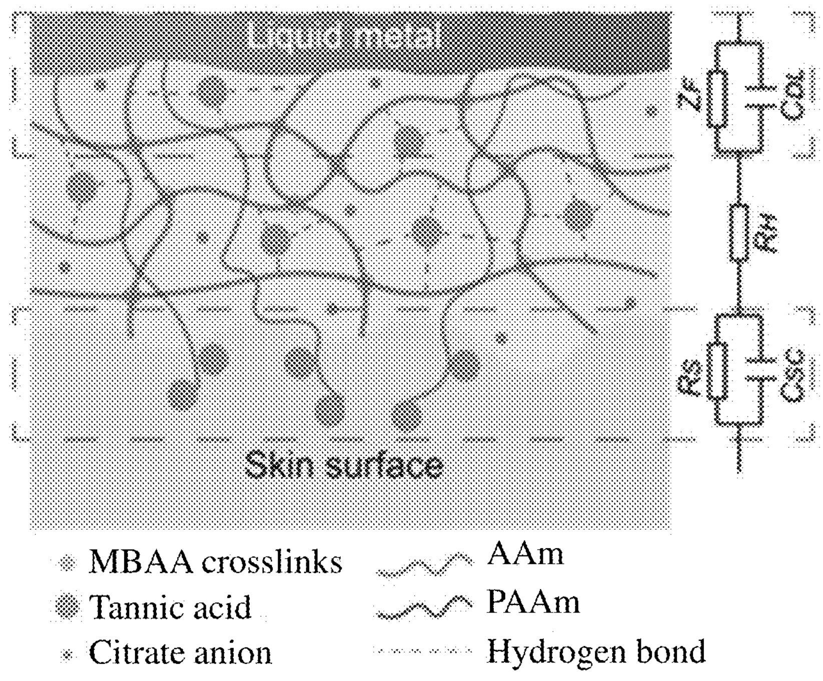
FIG. 3E is a schematic illustration showing chemical components and structures of the bioadhesive hydrogel, and the equivalent circuit of the electrical pathway in accordance with certain embodiments of the present disclosure.
Figure 3F:
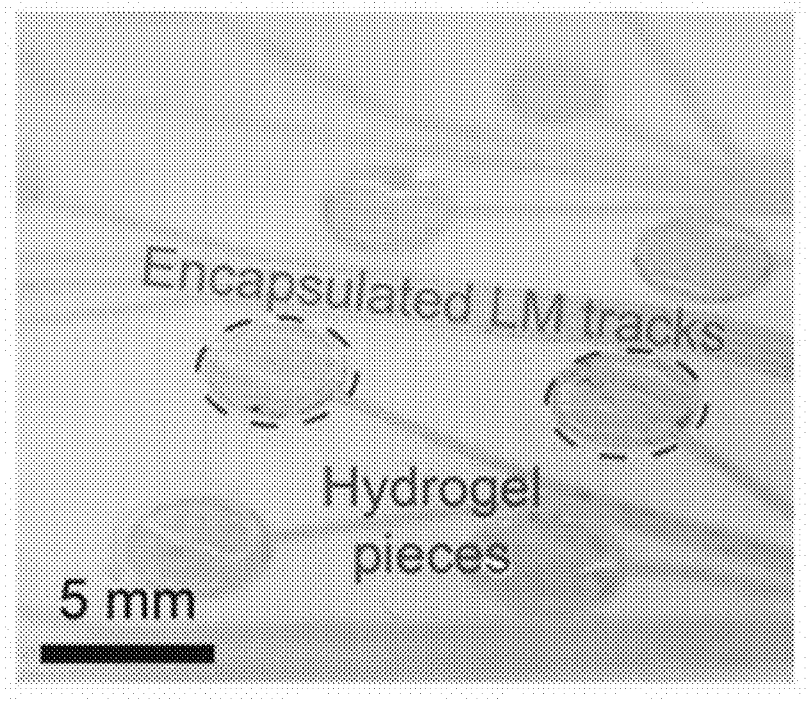
FIG. 3F is an optical photograph showing the hydrogel pieces that have cured and fixed on the encapsulated LM electrodes in accordance with certain embodiments of the present disclosure.

FIG. 3E is a schematic illustration showing chemical components and structures of the bioadhesive hydrogel, and the equivalent circuit of the electrical pathway in accordance with certain embodiments. $Z_F$ stands for Faradaic impedance. $C_{DL}$ is the electric double layer capacitance. $R_H$ is the resistance of the hydrogel. $R_S$ is the resistance of the skin, and $C_{SC}$ represents the capacitance of the stratum corneum. As the bioadhesive hydrogel provides a large $C_{DL}$ and $C_{SC}$ owing to the well bonding in both sides, the overall interface impedance can be lower than that for the prior art systems. FIG. 3F is an optical photograph showing the hydrogel pieces that cured and fixed on encapsulated LM electrodes in accordance with certain embodiments.

The low LM-hydrogel interfacial impedance has been validated by electrochemical impedance spectroscopy (EIS) test, which, according to certain embodiments, has an areal impedance value around or lower than 10 k $\Omega \cdot cm^2$ across the frequency spectrum from $10^0$~$10^3$ Hz and lower than 100 $\Omega \cdot cm^2$ in frequency range higher than $10^3$ Hz. The interfacial impedance is closely related to the size of the LM-hydrogel, as its size varies for adapting different thresholds. Typically, the diameters of the hydrogels used in tests are 2 mm, 4 mm and 6 mm. The thickness is typically 1 mm. Owing to functional components like tannic acid and polyacrylamide (PAAm), strong skin adhesion and robust bonding with LM is achieved through multiple dynamic interactions (e.g., hydrogen bond, Schiff-base/Michael addition reaction, cation-π interaction, metal coordination) and physical entanglement (e.g., long polymeric chains of PAAm) (FIG. 3E). As a result, the total impedance of the LM-hydrogel-skin interface is significantly lower than that of dry electrodes (i.e., Au) and commercial gel with the same size. Even when stretched to 100%, the impedance remains low, which is around or lower than 100 k $\Omega \cdot cm^2$ across the frequency spectrum from $10^0$~$10^3$ Hz and lower than 10 k $\Omega \cdot cm^2$ in frequency range higher than $10^3$ Hz. The lowered impedance allows high maximum current to pass through.

Figure 4A:
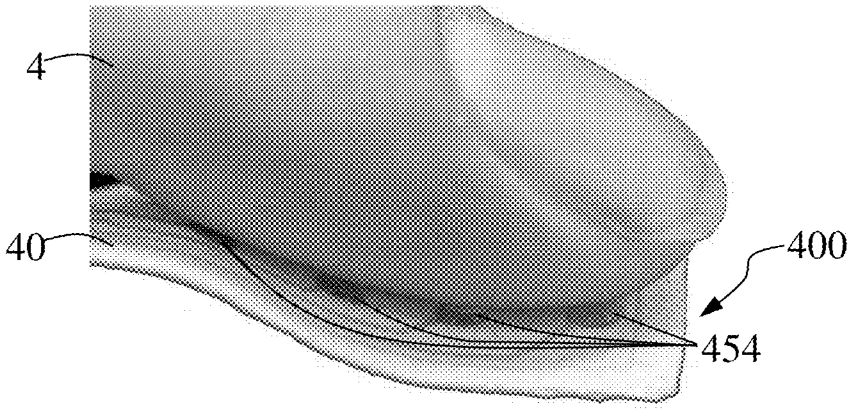
FIG. 4A depicts an optical photograph showing the strong adhesion between small pieces of a bioadhesive hydrogel and both skin and substrate, which keeps the BWHI tightly adhered to the hand during use in accordance with certain embodiments of the present disclosure.
Figure 4B:
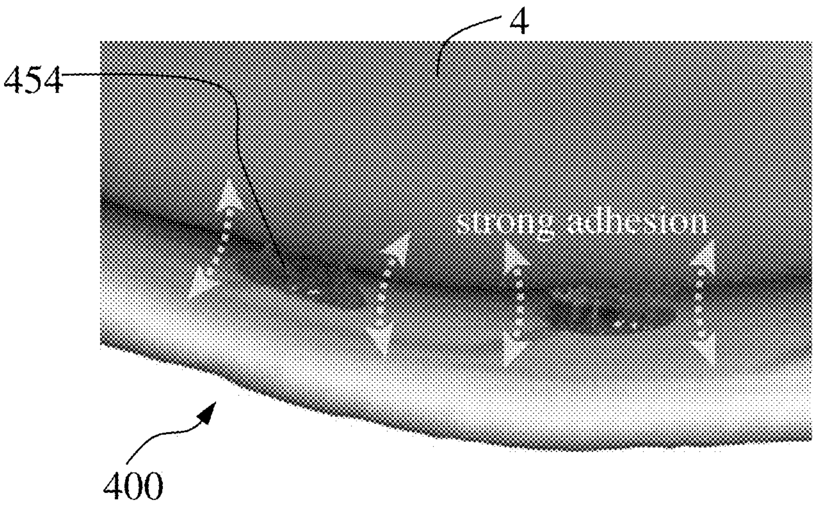
FIG. 4B depicts an optical photograph showing the strong adhesion between small pieces of a bioadhesive hydrogel and both skin and substrate of FIG. 4A from an enlarged view.
Figure 4C:
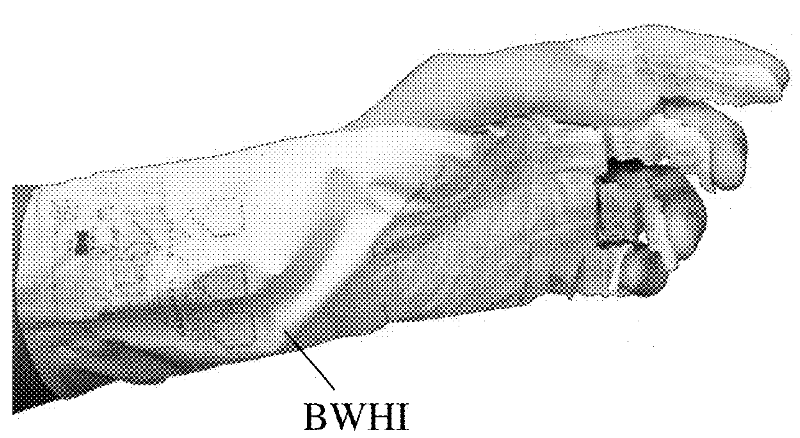
FIG. 4C depicts an optical photograph showing that the BWHI is attached to the palmar side of a user's hand and the user poses gestures to bend the device, while not affecting its normal use in accordance with certain embodiments of the present disclosure.
Figure 4D:
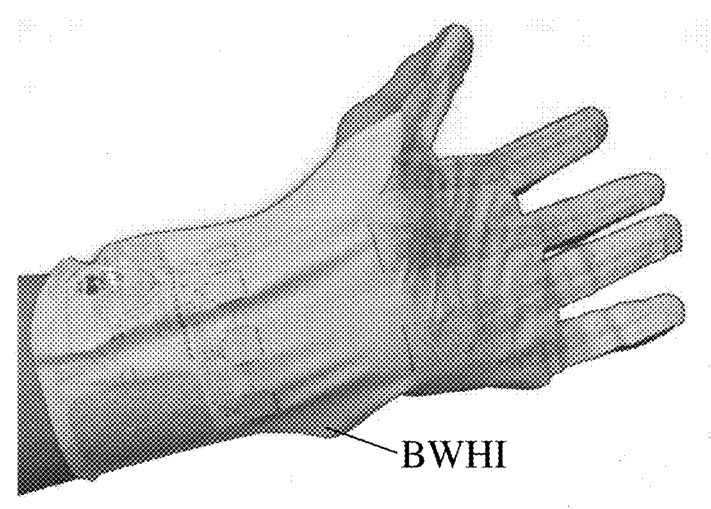
FIG. 4D depicts an optical photograph showing that the BWHI is attached to the palmar side of the user's hand of FIG. 4C, where the users poses gestures to stretch the device, while not affecting its normal use.
Figure 4E:
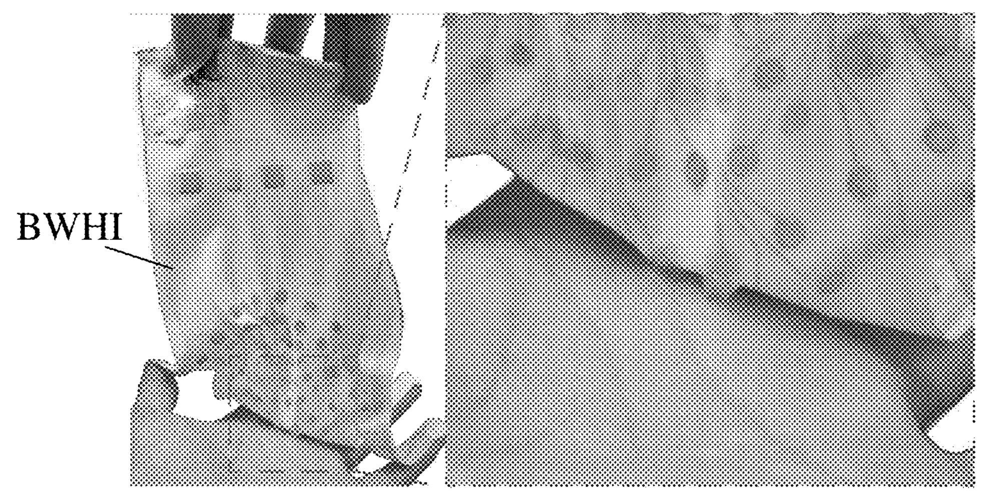
FIG. 4E depicts optical photographs showing the interface between the BWHI and a user's hand skin after exercising for 30 minutes, where the hand keeps dry, in accordance with certain embodiments of the present disclosure.

Referring to FIGS. 4A, 4B, 4C, 4D, 4E, it has been demonstrated that the breathable and bioadhesive properties endow the BWHI with excellent wearing comfort. As shown in FIGS. 4A and 4B, the BWHI 400 comprises a substrate 40 and hydrogel electrodes 454 that adhere to both the substrate 40 and the skin of a user's finger 4. The BWHI can stick or attached to the skin of hand tightly during use and will not peel off simply by the bioadhesive nature of hydrogel electrodes themselves. This is also owing to the softness and light weight of the BWHI system. The softness and elastomeric nature of the BWHI system also allows it to conform to the skin and being deformed (e.g. bent in FIG. 4C and stretched in FIG. 4D) together with the hand, without affecting the functions and performances. The excellent permeability of fiber mat substrate allows the moisture and sweat secreted by the hand to evaporate, which not only ensures the normal thermal equilibrium of the hand, but also keeps the skin interface dry (without sweat/moisture accumulation, FIG. 4E). This prevents the hand from inflammation, itchiness or unstable feedback experience that can be induced by skin occlusion.

Figure 5A:
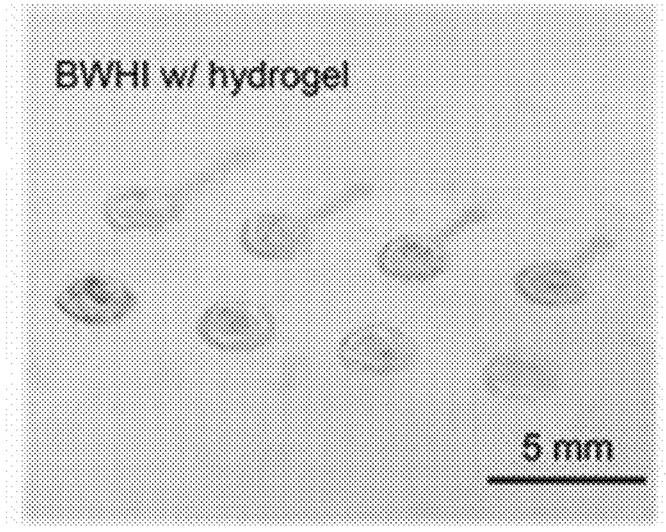
FIG. 5A depicts an optical photograph of the finger part of the BWHI, with 8 hydrogel pieces array printed on LM electrodes in accordance with certain embodiments of the present disclosure.
Figure 5B:
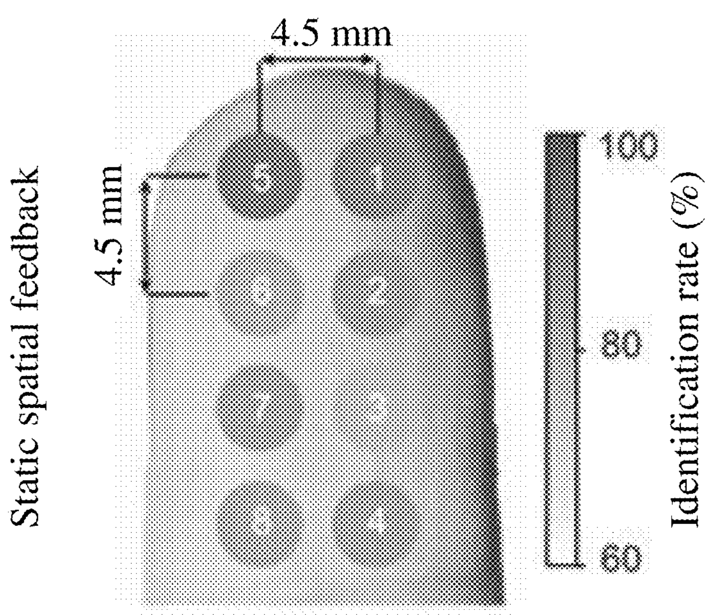
FIG. 5B is a schematic illustration showing the distribution of 8 stimulation sites on the fingertip and the rough position identification rates of them in static feedback test in accordance with certain embodiments of the present disclosure.
Figure 5C:
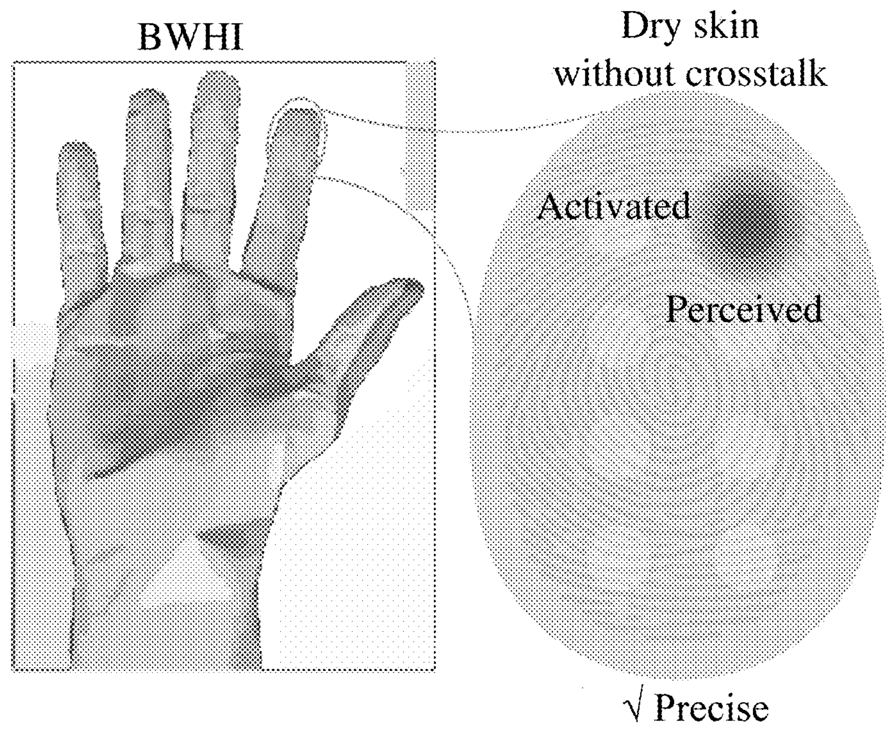
FIG. 5C is a schematic illustration of a feedback perception of the permeable BWHI, where the BWHI offers a dry skin interface without crosstalk and thereby the current is focused and the positions of the activated channels can be precisely perceived in accordance with certain embodiments of the present disclosure.
Figure 5D:
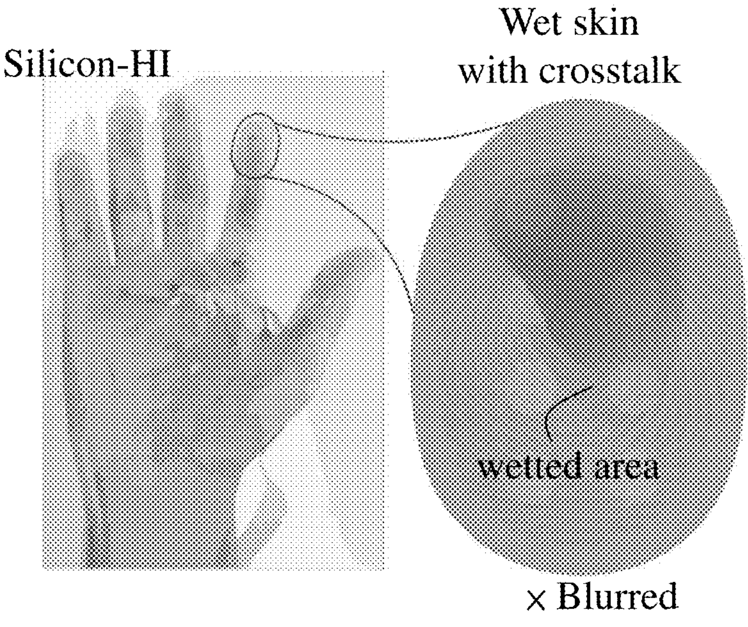
FIG. 5D is a schematic illustration the impermeable Silicone-HI, where the impermeable device results in wet skin interface and crosstalk among channels, and thereby the current is distributed and the sensation is blurred, in accordance with certain embodiments of the present disclosure.
Figure 5E:
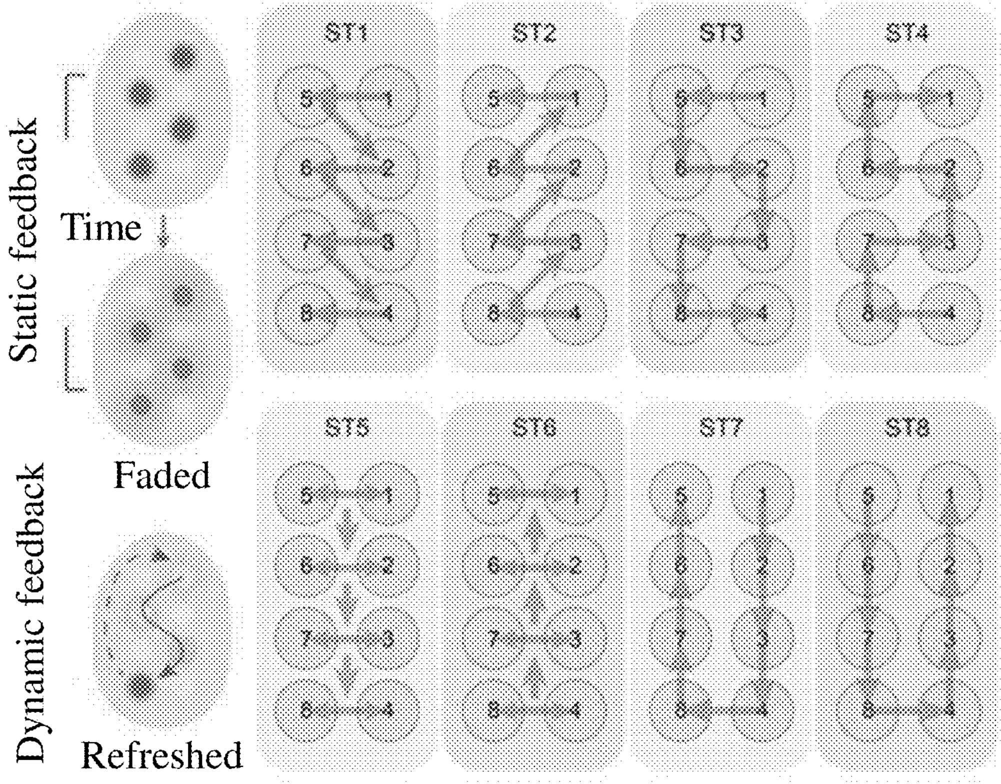
FIG. 5E is a schematic illustration of the spatiotemporal (ST) dynamic feedback for the fingertip in accordance with certain embodiments. As the sensation induced by the static feedback will gradually fade away, the spatiotemporal dynamic feedback can refresh the sensation because of the frequently moving of the stimulated position. 8 examples of ST feedback patterns are provided and it has been demonstrated that they are clearly distinguishable.
Figure 5F:
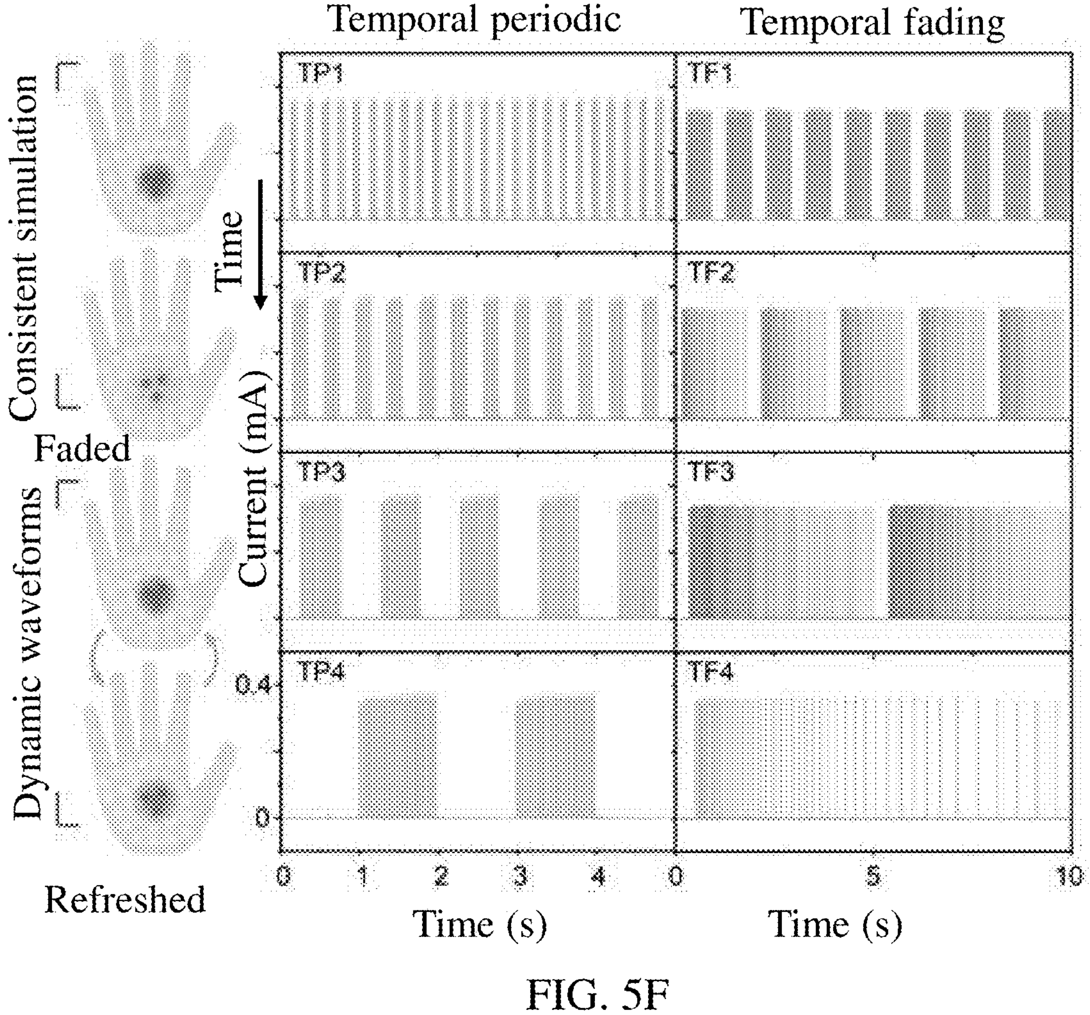
FIG. 5F is a schematic illustration of the temporal dynamic feedback. As the palm cannot distinguish spatial information with high resolution, the temporal periodic (TP) and temporal fading (TF) waveforms are utilized for conveying clearly distinguishable information encoded in the period or frequency changes to the palm.

Referring to FIGS. 5A, 5B, 5C, 5D, 5E and 5F, the BWHI can provide precise feedback with a high spatial resolution. Eight channels of electrodes are provided on each fingertip part of BWHI (FIG. 5A) and have been demonstrated to provide spatial recognizing accuracy of over 80% on all channels (FIG. 5B). During testing, sweating is observed to decrease identification accuracy. Tests have been conducted when BWHI and an impermeable silicone haptic interface (Silicone-HI) are worn for 30 minutes (FIGS. 5C and 5D respectively). As can be seen, when the BWHI is used (FIG. 5C), no crosstalk is observed and the skin remains dry after the wearing. The channels can be precisely identified. When the Silicone-HI is used (FIG. 5D), crosstalk and wetted area appear. The skin sensation becomes blurred after the wearing, and it is difficult to correctly recognize the channels. That is, the BWHI group maintains high accuracy, while the Silicone-HI group shows blurry/vague recognition result after long-term wearing, reflected in decreased identification rate of 53.8%. The reason for this decreasing could be the increased moisture in silicone-covered skin which worsens the crosstalk among adjacent channels. Thus, the excellent permeability of BWHI contributes to maintaining effective precise feedback in long-term use. It has also been found that the static feedback on unchanging positions always seems to result in a fading sensation with time. Hence, different spatiotemporal patterns are programmed for distinguishing (e.g. ST 1~8, FIG. 5E), where individual channels are sequentially activated and shut down in order to keep stimulated sites moving and keep the sensation refreshed. Compared to the static spatial feedback, the individual average identification rates show significant improvements, which demonstrates that spatiotemporal dynamic feedback provides more information and is much easier to precisely distinguish. Palm has higher thresholds of two-point discrimination due to the lower innervation density of mechanoreceptors; thus, fine patterns of spatiotemporal scanning may not be accurately perceived, and therefore lead to confusion in received information. To enhance the conveyance of tactile information beyond position and strength, consistent stimulation is prepared with encoding information into dynamic cycling temporal stimulation waveforms. For example, for shorter timescale (≤2 s), temporal periodic dynamic modes (TP 1~4) are developed, which alters the on and off states of stimulation with different periods. However, for longer time scales (2~10 s), the perception intensity may fade despite consistent current strength. To address this, temporal fading dynamic modes (TF 1~4) are developed, featuring gradually increasing pulse intervals, and returning to densely fired pulses at the start of next period. This sudden frequency change is clearly perceptible and keeps the sensation refreshed. All these dynamic modes are well recognized in all regions of the palm. As used herein, the term "static feedback" means the main parameters of stimulation current including current intensity, pulse width, period, and stimulation channel remains still during the whole feedback process. Oppositely, the term "dynamic feedback" means at least one of above-mentioned parameters keeps periodically changing during the whole feedback process. Spatiotemporal dynamic feedback patterns are generated by programming several pre-set sequences and durations of the output channels. The temporal periodic/fading dynamic modes are designed by programming the interval between pulses to decrease or increase periodically. These new modes can adapt the natural fading of the sensation in response to constant (chronic) stimulations, and periodically refresh the sensation by a sudden change of the pulse repetition frequency. In this way, the dynamic mode-induced tactile sensation can last for a longer time than the ones by static feedback and avoid numb sensations or increased thresholds during time.

As used herein, the term "avoid" or "avoiding" refers to any method to partially or completely preclude, avert, obviate, forestall, stop, hinder or delay the consequence or phenomenon following the term "avoid" or "avoiding" from happening. The term "avoid" or "avoiding" does not mean that it is necessarily absolute, but rather effective for providing some degree of avoidance or prevention or amelioration of consequence or phenomenon following the term "avoid" or "avoiding".

As used herein, being "flexible" of an object means that the object is capable of being flexed or bent without breaking.

As used herein, the term "identification rate" refers to the percentage of times when the user selects the correct option in the blinded random channel feedback test.

It will further be appreciated that any of the features in the above embodiments of the disclosure may be combined together and are not necessarily applied in isolation from each other. Similar combinations of two or more features from the above described embodiments or preferred forms of the disclosure can be readily made by one skilled in the art.

Unless otherwise defined, the technical and scientific terms used herein have the plain meanings as commonly understood by those skill in the art to which the example embodiments pertain. It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

What is claimed is:

1. A haptic apparatus for stimulating a skin of a user to provide haptic feedback to the user, the haptic apparatus comprising:

an elastomeric substrate layer; and multilayered electrical circuits comprising hydrogel electrodes for contacting the skin and electro-stimulating the skin to generate the haptic feedback, wherein the multilayered electrical circuits are arranged on the elastomeric substrate layer, thereby avoiding forming the multilayered electrical circuits on a printed circuit board.

2. The haptic apparatus of claim 1, wherein the multilayered electrical circuits are monolithically formed on the elastomeric substrate layer.

3. The haptic apparatus of claim 1, wherein the elastomeric substrate layer comprises an elastomeric fiber mat.

4. The haptic apparatus of claim 1, wherein the multilayered electrical circuits comprise patterned liquid metal (LM) traces.

5. The haptic apparatus of claim 4, wherein the hydrogel electrodes comprise:

LM pads disposed on the patterned LM traces; and a bioadhesive hydrogel disposed on the LM pads for establishing an electrically conducive path to the skin.

6. The haptic apparatus of claim 5, wherein the hydrogel electrodes further comprise a paste mask layer sandwiched between the LM pads and the bioadhesive hydrogel, and the paste mask layer is configured to allow the bioadhesive hydrogel to penetrate at least partially through the paste mask layer, thereby contacting the LM pads.

7. The haptic apparatus of claim 6, wherein the paste mask layer comprises fiber mat.

8. The haptic apparatus of claim 1, wherein the multilayered electrical circuits comprise:

a first circuit layer comprising first patterned liquid metal (LM) traces;

a second circuit layer comprising second patterned LM traces; and

LM interconnects for electrically connecting the first circuit layer and the second circuit layer.

9. The haptic apparatus of claim 8, wherein the LM interconnects comprise vertical interconnect accesses (VIAs), and the VIAs comprise fluidic LM for electrically contacting both the first patterned LM traces and the second patterned LM traces.

10. The haptic apparatus of claim 8, wherein the multilayered electrical circuits comprise electronic components disposed on the second circuit layer, and the electronic components electrically contact the second patterned LM traces through hybrid LM (hLM) solders.

11. The haptic apparatus of claim 10, wherein the hLM solders comprise:

fluidic LM electrically contacting the electronic components; and an oxidized LM (oLM) paste sandwiched between the fluidic LM and the second patterned LM traces, thereby to electrically connect the electronic components to the second circuit layer.

12. The haptic apparatus of claim 1, further comprising an elastomeric encapsulation layer for at least partially encapsulating the multilayered electrical circuits.

13. The haptic apparatus of claim 12, wherein the elastomeric encapsulation layer comprises an elastomeric fiber mat.

14. The haptic apparatus of claim 1, wherein the hydrogel electrodes comprise a plurality of channels, and the multilayered electrical circuits comprise a control circuit for generating pulsed voltage signals for feeding into the plurality of channels for stimulating the skin of the user.

15. The haptic apparatus of claim 14, wherein the control circuit comprises:

a power management module for generating a regulated voltage;

a voltage booster module for boosting up the regulated voltage to yield a boosted voltage;

a plurality of multiplexers for controllably switching on and off the boosted voltage to generate pulsed voltage signals; and a microcontroller unit (MCU) configured to at least control the plurality of multiplexers in switching the boosted voltage for generating an individual pulsed voltage signal with a desired pulse frequency and a desired duty cycle.

16. The haptic apparatus of claim 15, wherein the power management module comprises:

a battery for providing a battery supplied electrical voltage; and a regulator for regulating the battery supplied electrical voltage to the regulated voltage.

17. The haptic apparatus of claim 16, wherein the battery is a rechargeable battery, and the power management module further comprises a QI wireless charging module for recharging the rechargeable battery.

18. The haptic apparatus of claim 15, wherein the control circuit further comprises a current control module controllable by the MCU for monitoring and limiting a return current received by a common electrode from the user to avoid the user from getting an electric shock.

19. The haptic apparatus of claim 18, wherein the current control module comprises a current mirror that electrically connects to the MCU through either an operational amplifier or a digital-to-analog converter.

20. The haptic apparatus of claim 1, wherein the hydrogel electrodes have a highest electrode density of 2.26 units/$cm^2$.

* * * * *